United States Patent [19]

Hopp et al.

[11] Patent Number: 5,371,013
[45] Date of Patent: Dec. 6, 1994

[54] PROCESS FOR THE PREPARATION OF SUBSTITUTED METHOXYPHENOLS AND MICROORGANISMS SUITABLE FOR THIS PURPOSE

[75] Inventors: Rudolf Hopp, Holzminden; Jürgen Rabenhorst, Höxter-Stahle, both of Germany

[73] Assignee: Haarmann & Reimer GmbH, Holzminden, Germany

[21] Appl. No.: 104,832

[22] Filed: Aug. 10, 1993

[30] Foreign Application Priority Data

Aug. 17, 1992 [DE] Germany .......................... 4227076

[51] Int. Cl.⁵ .......................... C12N 1/20; C12P 7/22; C12P 7/42; C12P 7/24
[52] U.S. Cl. ................. 435/253.3; 435/147; 435/156; 435/874
[58] Field of Search ............ 435/156, 147, 253.3, 435/874

[56] References Cited

PUBLICATIONS

Database WPI, AN 90-278836, Derwent Publications Week 9037, JP 2195871 A, Hasegawa KK, "Novel microbe and enzyme-comprises bacterial . . . "; 1 page.
Database WPI, AN 93-316614, Derwent Publications, Week 9340, JP 5227980 A, Takasago Perfumery Co, Ltd., "Prepn. of vanillin, coniferyl-alcohol and . . . "; 1 page.
Agricultural and Biological Chemistry, vol. 47, Nov. 1983, cover page + 2nd page and pp. 2639–2640; "Initial Steps of Eugenol Degradation Pathway of a Microorganism", K. Tadasa et al.
Database WPI, AN 90-285861, Derwent Publications, Week 9038, JP 2200192 A, Hasegawa KK, "Prepn. of Benzaldehyde Deriv. . . . "; 2 pages.
Tadasa et al., Agric. Biol. Chem., Apr. 20, 1983, p. 2639.

*Primary Examiner*—Herbert J. Lilling
*Attorney, Agent, or Firm*—Sprung Horn Kramer & Woods

[57] ABSTRACT

Ferulic acid, vanillic acid, coniferyl alcohol and coniferyl aldehyde can be prepared from eugenol with the aid of a new Pseudomonas species.

1 Claim, No Drawings

PROCESS FOR THE PREPARATION OF SUBSTITUTED METHOXYPHENOLS AND MICROORGANISMS SUITABLE FOR THIS PURPOSE

The invention relates to a process for the preparation of substituted o-methoxyphenols from eugenol or eugenol-containing mixtures with the aid of microorganisms, and to bacteria which are suitable for this process.

Substituted methoxyphenols, such as, for example, coniferyl alcohol and coniferyl aldehyde, can be used as aroma substances. Nevertheless, coniferyl alcohol and especially coniferyl aldehyde are not available at all in relatively large quantities. There was therefore the need for a process which can be used economically on an industrial scale.

Other methoxyphenols are suitable as advantageous intermediate products for the preparation of various natural aroma substances. Thus, for example, the preparation of vanillin, inter alia, from ferulic acid is described (EP-A-453 368). Ferulic acid is already relatively expensive as a synthetic product. However, the preparation of natural aroma substances requires the use of natural starting materials. Natural ferulic acid, however, has not hitherto been available. It occurs merely in low concentrations in various plant materials—usually in bonded form (ester). A natural isolation from this is not economically viable. For vanillic acid also, no expedient natural source is known.

The breakdown of eugenol via coniferyl alcohol and ferulic acid using a Pseudomonas sp. has already been described once in the literature (K. Tadasa and H. Kayahara, Agric. Biol. Chem., 47, 2629–2640, 1983). On the basis of the description, it must be another species; the deciding factor is, however, that the strain has not been deposited and is therefore not available for reproduction of the work.

A new Pseudomonas sp. which, surprisingly, is capable of converting eugenol into ferulic acid, vanillic acid, coniferyl alcohol and coniferyl aldehyde has now been isolated from a soil sample from eastern Java/Indonesia. Eugenol is a relatively inexpensive constituent of natural oil of cloves.

The invention thus relates to the new species Pseudomonas sp., the strains having been deposited at the Deutsche Sammlung für Mikroorganismen und Zellkulturen GmbH (German Collection of Microorganisms and Cell Cultures GmbH) in Braunschweig under the numbers DSM 7062 and DSM 7063.

| Taxonomic description of the species | |
| --- | --- |
| Cell form: | Rod-shaped |
| Width (μm) | 0.5–0.7 |
| Length (μm) | 1.2–2.5 |
| Motility | + |
| Flagella | polar 1 |
| Gram reaction | negative |
| Lysis by 3% KOH | + |
| Aminopeptidase (Cerny) | + |
| Spores | − |
| Oxidase | + |
| Catalase | + |
| Growth | |
| anaerobic | − |
| 37/41° C. | +/+ |
| pH 5.6 | + |
| MacConkey agar | + |
| SS agar | + |
| Cetrimide agar | + |

| -continued | |
| --- | --- |
| Taxonomic description of the species | |
| Pigments | |
| non-diffusing | − |
| diffusing | − |
| fluorescent | − |
| pyocyanin | − |
| Gas from glucose | − |
| Acid from (ASS) | |
| glucose | + |
| fructose | + |
| ADH | + |
| ONPG | − |
| VP | − |
| Indole | − |
| NO₂ from NO₃ | + |
| Phenyldeaminase | − |
| Laevan from sucrose | − |
| Urease | − |
| Hydrolysis of | |
| starch | − |
| casein | − |
| DNA | − |
| Tween 80 | − |
| Aesculin | − |
| Growth promoter requirement | − |
| Substrate utilisation | |
| acetate | + |
| adipate | + |
| azelate | + |
| caprate | + |
| citrate | + |
| glycolate | − |
| lactate | + |
| laevulinate | + |
| malate | + |
| malonate | − |
| mucate | + |
| sebacate | + |
| suberate | − |
| phenylacetate | + |
| L-arabinose | − |
| fructose | + |
| glucose | + |
| mannose | − |
| xylose | − |
| galactose | − |
| trehalose | − |
| sucrose | − |
| saccharate | − |
| mannitol | − |
| inositol | − |
| gluconate | + |
| alanine | + |
| hydroxybutyrate | + |
| geraniol | + |
| benzoylformate | − |

Slight individual variations, especially in the substrate utilisation spectrum, are usual within a species and cannot be excluded.

The invention furthermore relates to a process for the preparation of compounds of the formula

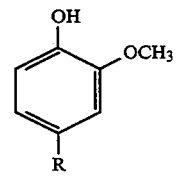

wherein
R denotes —COOH, —CH=CH—COOH, or —CH=CH—CH₂OH or —CH=CH—CHO,
from eugenol

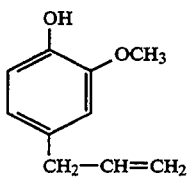

in the presence of the new Pseudomonas sp. or enzymes thereof or of microorganisms with genetic material from the new Pseudomonas sp. which encodes the structure and regulator genes for the enzymes which are active in this reaction.

Eugenol can also be employed as a mixture with other components, for example in the form of oil of cloves. The new species Pseudomonas sp. to be used according to the invention can be cultured in the usual culture media. These culture media can be synthetic, semi-synthetic or complex, and can comprise carbon sources, nitrogen sources, inorganic salts and, if appropriate, trace elements and vitamins.

Carbon sources which can be used are, for example, sugars, such as glucose, sugar alcohols, such as glycerol, organic acids, such as citric acid, or complex mixtures, such as malt extract, yeast extract, casein or casein hydrolysate.

Examples of suitable nitrogen sources are inorganic nitrogen sources, such as nitrates and ammonium salts, and organic nitrogen sources, such as yeast extract, soya flour, cotton seed flour, casein, casein hydrolysate, wheat gluten and corn steep liquor.

Examples of organic salts which can be used are, inter alia, sulphates, nitrates, chlorides, carbonates and phosphates of sodium, potassium, magnesium, calcium, zinc and iron.

The substrate can be added at the start of incubation or during or after the conclusion of growth, all at once or distributed over a longer period of time. The amount of eugenol is advantageously chosen such that the concentration of the compound in the culture broth does not exceed 30 g/l, preferably 5 g/l. The course of the oxidation can be monitored by determination of the starting material and of the products in the culture broth by means of high pressure liquid chromatography. When the optimum amount of the desired substances has formed, these can be isolated from the culture broth by known physical methods, such as extraction, distillation or chromatography, and purified by further steps.

The culture temperature is preferably in the range from 10° to 48° C., particularly preferably in the range from 16° to 37° C. The pH of the medium is preferably 3 to 9, in particular 4 to 8. Culture can be carried out for example, in suitable shaking apparatuses or in fermenters with a mixing device. Adequate aeration must be ensured during culture. Culture can be carried out batchwise, semi-continuously or continuously. The culture duration until a maximum amount of product is achieved is between 4 and 240 hours. To protect the microorganisms from the toxic action of the eugenol, it may be advantageous to add adsorbents for the substrate, for example active charcoal or adsorber resins, to the culture media.

By choosing suitable process parameters, it is possible to obtain individual substances of those mentioned above as the main components of the reaction.

EXAMPLES

Preparation of the inoculum 100 ml of nutrient broth were introduced into a 500 ml conical flask and were then sterilised at 121° C. for 20 minutes. After cooling, the flask was inoculated with a culture of Pseudomonas sp. nov. DSM 7062 or DSM 7063 from an agar plate using an inoculation loop. The culture was incubated on a rotary shaker at 27° C. and 120 revolutions per minute. After 17 hours, this culture was used for inoculating the production medium. Example 1

Production in a shaking flask

In each case 100 ml medium (4 g $K_2HPO_4$, 1 g $NaH_2PO_4$, 0.5 g yeast extract, 0.2 g NaCl, 0.2 g $MgSO_4 \times 7 H_2O$, 0.05 g $CaCl_2$, 1000 ml water, pH 7.25) were introduced into nine 500 ml conical flasks and were then steam-sterilised at 121° C. for 20 minutes. After cooling, the flasks were inoculated with in each case 5 ml of a culture of DSM 7063. The cultures were incubated on a rotary shaker at 27° C. and 120 revolutions per minute. Immediately after the inoculation, 500 ppm of eugenol were added, and a further 500 ppm were added after 4.5 hours and in each case a further 1000 ppm after 9, 24 and 32.75 hours. After 54 hours, the fermentation was terminated, the flasks were autoclaved, the culture broth in the flasks was combined and the cell mass was separated off. According to analyses by high pressure liquid chromatography, the content of ferulic acid in the culture broth was 1280 ppm, corresponding to a conversion of 32% of theory. The content of coniferyl alcohol was 225 ppm and the content of vanillic acid was 131 ppm.

Isolation of the ferulic acid 810 ml of the culture filtrate obtained in Example 1 were brought to pH 4.0 with 1N HCl and extracted once with the same volume of ethyl acetate. The organic phase was separated off and the solvent was removed in vacuo on a rotary evaporator. A precipitate of 1.31 g, which contained 71% ferulic acid, was obtained. This corresponds to a recovery of 90%.

Example 2

Production in a 10 l fermenter 10 l of culture medium (100 g of malt extract, 40 g of glucose, 20 g of yeast extract, 10 000 ml of water, pH 7.3) were sterilised in a fermenter and, after cooling, were inoculated with 0.5 l of an inoculum of DSM 7063. The culture conditions were: 32° C., 200 revolutions per minute, 8 l air/minute. Immediately after the inoculation, 1000 ppm of eugenol were added, 500 ppm were added after 7 hours, and in each case a further 1000 ppm were added after 10.5, 16, 22, 25 and 28 hours. In addition, the air was reduced to 4 l of air/minute after 25 hours.

The fermentation was discontinued after 32.5 hours. The concentration of the individual components was:

| Ferulic acid | 2365 ppm | (31% of theory) |
|---|---|---|
| Coniferyl alcohol | 1458 ppm | (20% of theory) |
| Vanillic acid | 1314 ppm | (20% of theory) |
| Coniferyl aldehyde | 11 ppm | |

At the end of the process, 270 ppm (4%) of unreacted eugenol were still present.

Example 3

Production of vanillic acid in a 10 l fermenter 10 l of culture medium ($KH_2PO_4$ 16 g; $Na_2HPO_4$ 30 g; $NH_4Cl$ 5.3 g; $MgSO_4 \times 7$ $H_2O$ 1 g; $CaCl_2 \times 0.7$ g; yeast extract 10 g, deionised $H_2O$ to 10 l; pH 7.0) were sterilised in a fermenter and, after cooling, were inoculated as in Example 2. The culture conditions were: 27° C., 200 revolutions per minute, 4 l air/minute. Immediately after the inoculation, 1000 ppm of eugenol were added, and in each case a further 1000 ppm were added after 12, 20, 23.5, 28.5 and 36 hours.

After 99 hours, the fermentation was stopped. The concentration of vanillic acid was 3.25 g/l, corresponding to a conversion of 52.9% of theory.

Example 4

Production of coniferyl alcohol 10 l of nutrient broth were sterilised in a fermenter and, after cooling, were inoculated with an inoculum of DSM 7063 which was 24 hours old. The culture conditions were 27° C., 400 revolutions per minute, 4 l air/minute. After 15 hours, this culture was transferred, under sterile conditions, to a fermenter containing 190 l medium according to Example 1 and was cultured at 27° C., 200 revolutions per minute and 40 l of air/minute. 1000 ppm eugenol were added at the start of the fermentation, 250 ppm were added after 7.5 hours, 1000 ppm after 14 hours, 250 ppm after 14.5 hours and after 23.5 hours, 1405 ppm during the next 6 hours from the 25th hour onwards and 2590 ppm during the next 15.5 hours after the 32nd hour. A total of 6745 ppm of eugenol was added over a period of 47.5 hours.

The yield of coniferyl alcohol was 3226 ppm. This corresponds to 43.5% of theory. In addition, a further 1738 ppm (25% of theory) of ferulic acid were also obtained, as well as 12 ppm of coniferyl aldehyde and 8 ppm of vanillic acid. At the end of the process, 496 ppm (7.3%) of unreacted eugenol were still present.

Example 5

Production of ferulic acid 10 l culture medium (40 g of $K_2HPO_4$, 10 g of $NaH_2PO_4$, 5 g of casein hydrolysate, 2 g of NaCl, 2 g $MgSO_4 \times 7$ $H_2O$, water to 10 l, pH 7.25) were sterilised in a fermenter and, after cooling, were inoculated with 0.5 l of the inoculum of DSM 7063. The culture conditions were: 27° C., 300 revolutions per minute, 4 l of air/minute. Immediately after the inoculation, 1000 ppm of eugenol were added, 500 ppm were added after 6.5 hours, and in each case a further 1000 ppm were added after 8.5; 13.5; 19; 23.5; 26.5; 30.5; 37.5; and 45.5 hours. In each case 2 g of casein hydrolysate were additionally added after 30.5 and 50 hours.

The fermentation was terminated after 75 hours. The concentration of ferulic acid was 5.8 g/l, corresponding to a conversion of 51.6% of theory.

On fermentation of DSM 7062 at 32° C., the concentration of ferulic acid after 78 hours was 6.7 g/l; since 13.9 g/l of eugenol are employed, this corresponds to 41% of theory.

We claim:

1. A biologically pure culture of the microorganism Pseudomonas sp. nov. DSM 7062 or DSM 7063.

* * * * *

UNITED STATES PATENT AND TRADEMARK OFFICE
CERTIFICATE OF CORRECTION

PATENT NO. : 5,371,013
DATED : December 6, 1994
INVENTOR(S) : Hopp, et al.

It is certified that error appears in the above-indentified patent and that said Letters Patent is hereby corrected as shown below:

Title Page     Insert -- U.S. PATENT DOCUMENTS: 5,128,253 7/1992, Labud, et al.; 3,817,830, 6/1974, Hegeman, et al. --.

Title Page     Insert -- FOREIGN PATENT DOCUMENTS: 0453368, 4/1991, European Pat. Off. --

Signed and Sealed this

Twenty-sixth Day of March, 1996

Attest:

BRUCE LEHMAN

*Attesting Officer*     *Commissioner of Patents and Trademarks*